United States Patent [19]

Gross

[11] B 4,079,029

[45] Mar. 14, 1978

[54] ABSORBENT ARTICLES MADE FROM LATEXES OF CARBOXYLIC SYNTHETIC POLYELECTROLYTE CONTAINING N-SUBSTITUTED ACRYLAMIDE CROSSLINKING AGENT

[75] Inventor: James Richard Gross, Lake Jackson, Tex.

[73] Assignee: The Dow Chemical Company, Midland, Mich.

[21] Appl. No.: 494,450

[22] Filed: Aug. 5, 1974

[44] Published under the second Trial Voluntary Protest Program on February 17, 1976 as document No. B 494,450.

[51] Int. Cl.$^2$ .............................................. C08L 25/08
[52] U.S. Cl. .................. 260/29.6 TA; 260/29.6 H; 260/29.6 HN; 260/33.4 R; 260/80.73; 128/156; 428/255; 428/264; 526/240
[58] Field of Search ............... 260/29.6 HN, 29.6 TA, 260/33.4 R, 29.6 H

[56] References Cited

U.S. PATENT DOCUMENTS 3,860,549  1/1975  Sekmakos .................. 260/29.6 TA
3,957,710  5/1976  Rohmann .................. 260/29.6 TA

FOREIGN PATENT DOCUMENTS 950,153  2/1964  United Kingdom
1,209,333  10/1970  United Kingdom Primary Examiner—Harry Wong, Jr.
Assistant Examiner—Peter F. Kulkosky
Attorney, Agent, or Firm—Benjamin G. Colley

[57] ABSTRACT

Water swellable absorbent articles, made from latexes having a copolymerized crosslinker, together with methods for their preparation, and a composition containing a copolymerized crosslinker useful to make said articles are disclosed. The articles are crosslinked by heating and/or removing substantially all of the water from the precursor composition.

The absorbent articles are useful as surgical sponges, diapers, tampons, meat trays, bath mats and the like.

4 Claims, No Drawings

ABSORBENT ARTICLES MADE FROM LATEXES OF CARBOXYLIC SYNTHETIC POLELECTROLYTE CONTAINING N-SUBSTITUTED ACRYLAMIDE CROSSLINKING AGENT

BACKGROUND OF THE INVENTION

This invention relates to water swellable absorbent articles made from crosslinked polyelectrolytes, methods for their preparation, and to a composition consisting of polyelectrolytes containing a copolymerized crosslinker which is useful to make absorbent articles.

It is known from U.S. Pat. Nos. 3,669,103 and 3,670,731 that cross-linked polymeric sorbents can be sandwiched between flexible supports to achieve disposable diapers or dressings.

It is further known from U.S. Pat. Nos. 2,988,539 and 3,393,168; 3,514,419 and 3,557,067 that water swellable cross-linked carboxylic copolymers can be prepared. However, these prior art copolymers are all crosslinked during copolymerization or crosslinked after polymerization with subsequent neutralization of the carboxylic acid groups to form water swellable polyelectrolytes and hence these prior art polyelectrolytes cannot be crosslinked in situ as a coating on a substrate or as a flexible film thereof.

It is known from Ser. No. 468,794, filed Apr. 9, 1974 and Ser. No. 450,650, filed Mar. 13, 1974 that water swellable cured articles can be made from polyelectrolytes that have been crosslinked after polymerization with the addition of special crosslinking compounds prior to the heating or curing step.

The present invention is an improvement over these inventions in that the crosslinking agent is built into or copolymerized with the polyelectrolytes during the polymerization. The advantage of this invention is that only a single solution needs to be sent to users and the chance of operator error in the mixing of the crosslinking agents is eliminated.

SUMMARY OF THE INVENTION

The present invention comprises a latex derived composition which is useful to form water swellable articles of a carboxylic type synthetic polyelectrolyte which consists of a solvent such as lower alcohols, water, or mixtures thereof, about 5 to about 60 percent, preferably about 15 to about 40 percent by weight based on the solvent of a carboxylic copolymer which contains in the copolymer (A) about 25 to about 98 percent by weight based on the total weight of the copolymer of an alkali metal salt of an olefinically unsaturated monocarboxylic acid, (B) about 2 to about 50 percent by weight of an olefinically unsaturated monocarboxylic acid, (C) about 25 to about 60 percent by weight of an alkyl ester of an olefinically unsaturated monocarboxylic acid and (D) about 0.3 to about 5.0 percent by weight of an N-substituted acrylamide or methacrylamide wherein the substituent group is a hydroxymethylene or an alkoxymethylene group having 1–8 carbons in the alkyl group.

The invention further comprises methods of making discrete films, absorbent articles, particulates, fibers, and the products of these processes wherein the above composition on various substrates, is heated to a temperature greater than about 30°C. and preferably from about 90° to about 150°C. The use of these elevated temperatures is advantageous to accelerate the crosslinking and drying of the polyelectrolyte.

In order to obtain very high production rates of absorbent articles, it may be desirable to replace part or nearly all of the water in the polyelectrolyte solution with a lower alcohol such as methanol or ethanol. This substitution results in lower solution viscosities at a given percent solids and promotes rapid drying.

The final products of the present invention are thus water swellable and are useful whereever aqueous solutions need to be absorbed. Examples of the diverse utilities are surgical sponges, catamenial tampons, diapers, meat trays, paper towels, disposable door mats, disposable bath mats and disposable litter mats for household pets.

DETAILED DESCRIPTION

The mechanism through which the polyelectrolytes of this invention cure themselves (i.e. without an added curing agent) involves the condensation of a pendant carboxylic acid group on one polymer chain with a substituted amide group on another polymer chain with the resulting elimination of a molecule of water or alcohol. This reaction is thermodynamically possible at any temperature but for all practical purposes only proceeds at elevated temperatures. Since the reaction is dependent on two separate species coming together in solution, the rate is concentration dependent and once the composition is applied to a substrate and evaporation of solvent begins, the rate of cross-linking accelerates. Applying heat at this time increases the rate even more.

If the crosslinking reaction is allowed to occur in the original solution as by heating or prolonged storage, the absorbent article of this invention cannot be fabricated. The solution will become progressively more viscous and stringy until it forms a continuous gel which cannot be spread, sprayed or spun.

Examples of useful alkyl acrylates are methyl acrylate, ethyl acrylate, propyl acrylate, hexyl acrylate and the like. Examples of useful alkyl methacrylates are butyl methacrylates, hexyl methacrylates, octyl methacrylate, decyl methacrylate and the like.

The foregoing polyacrylates are then dissolved in an aqueous alkali metal hydroxide solution. Generally the equivalents of hydroxide solution used are from about 30 to about 70 percent based on the molar concentration of polymerized monomer and the preferred amount is from about 40 to about 55 percent. In any event, the amount of hydroxide solution added is sufficient to convert or saponify some of the acrylate esters to alkali metal carboxylates and to neutralize the carboxylic groups of the polyacrylate used into alkali metal carboxylates so that the converted polyacrylate has about 30 to about 70 weight percent of alkali metal carboxylates.

The foregoing aqueous solution can be used per se to prepare the final products of this invention. However, it is sometimes advantageous to add various amounts of volatile monohydric alcohols to control the viscosity of the aqueous solutions and increase the rate of drying. Examples of useful monohydric alcohols are lower alkanols such as methyl alcohol, ethyl alcohol and propyl alcohol.

The N-substituted acrylamides that are useful in this invention have the following generic formula:
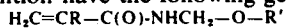

wherein R is selected from hydrogen or methyl and R' is hydrogen or an alkyl group of 1–8 carbons.

Examples of these N-hydroxymethyl or N-alkoxymethylene acrylamides or methacrylamides are N-methoxymethyl acrylamide,
N-propoxymethyl acrylamide,
N-isopropoxymethyl acrylamide,
N-ethoxymethyl acrylamide,
N-methylol acrylamide,
N-butoxymethyl acrylamide, and
N-tertiary butoxy methyl acrylamide,
N-isobutoxymethyl acrylamide,
N-octyloxymethyl acrylamide,
N-methoxymethyl methacrylamide
N-propoxymethyl methacrylamide
N-isopropoxymethyl methacrylamide,
N-ethoxymethyl methacrylamide,
N-methylol methacrylamide,
N-butoxymethyl methacrylamide,
N-tertiary butoxy methyl methacrylamide,
N-isobutoxymethyl methacrylamide and
N-octyloxymethyl methacrylamide.

In the method of making water swellable films by the present invention, the above composition of the polyelectrolytes having a pH range from 7 to 9 is acidified by adding organic or inorganic acids to a pH range 3 to 6 and spread on a flat plate or roller of metal, plastic, or other impervious substrate and heated to a temperature greater than 30°C. to crosslink the polyelectrolyte and drive off the excess water and/or alcohol. The film is then peeled off the plate or roller by a scraper to recover the intact film for subsequent storage or use.

It is sometimes desirable to add a small amount of a surfactant to the polyelectrolyte composition to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and ethylene oxide derivatives or alkylated phenols and the like.

Similarly, when an absorbent article is prepared, the article which is to be the substrate is coated with the acidified composition of the polyelectrolyte and then the coating is crosslinked. It is to be understood that for the purposes of this invention the coating step implies a complete coating or a discontinuous coating, thus when a fiberous substrate such as cellulose batting, paper, woven or non-woven cloth, and the like are used as the substrate, the composition can be applied in a discontinuous manner, i.e. in a pattern of large dots, squares, or grid lines to retain the inherent flexibility of the fiberous substrate and at the same time vastly improve its water absorbency. Wood pulp can be coated by slurrying it in the polyelectrolyte composition followed by a fluffing operation.

If desired, the water swellable film prepared as above can be used per se as the inner absorbent layer in baby diapers. It is sometimes advantageous that the film be disintegrated into flakes, strips or powders. This is accomplished by crushing or comminuting the film in a hammer mill, blenders, or the like. If long flat strips are desired, the film can be sliced widthwise with appropriate slicers.

In some instances, water swellable fibers are desired. These can be prepared by extruding the above composition of the polyelectrolytes into a bath comprising lower alkyl ketones such as acetone, methyl ethyl ketone, diethyl ketone and the like. Alcoholic compositions may be extruded into a non-aqueous coagulant such as chlorinated hydrocarbons, i.e. methylene chloride, perchloroethylene and the like. The soft extruded fibers are then removed from the bath by any convenient means such as a three or five roll cluster and carrier through a heated chamber at a temperature greater than about 30°C and preferably in the range from about 70° to about 150°C. to dry and to crosslink the polyelectrolyte fibers.

The absorbency of the crosslinked polyelectrolytes (grams solution gelled per gram of polyelectrolyte) is determined in the following manner using synthetic urine (0.27 N sodium chloride solution).

A 0.5 gram sample of a crosslinked polyelectrolyte is weighed into a 250 ml. beaker, a 0.27 N sodium chloride solution (150 ml.) is poured into the beaker and allowed to soak for 2 hours at room temperature, with occasional stirring. The swelled polyelectrolyte is then collected by filtration and the gel capacity is reported as grams of solution gelled per gram of polymer salt.

The following examples are presented solely to illustrate but not limit the invention.

EXAMPLE 1

Step 1 — Polymerization
  Part A
    230 g $H_2O$
    1.1 g sodium persulfate
    2.0 g Dowfax 2A-1 surfactant (disodium salt of dodecylated sulfonated phenyl ether)
  Part B
    167 g ethyl acrylate
    30 g methacrylic acid
    3 g N-isobutoxymethyl acrylamide (1.5 weight percent based on the monomer feed)
  Part C
    70 g $H_2O$
    1.3 g sodium bisulfite Part A was heated to 40°C. in a stirred 1000 ml. flask. All of Part C and 20 ml. of Part B was added with the remainder of Part B fed in over a period of 97 minutes while maintaining the temperature at 40° ± 1°C. The latex was digested for 30 minutes with heating to bring the final temperature to 80°C. Due to some coagulum formation, the actual percent solids of the latex was 36.6.

Step 2 — Neutralization and Saponification

A 20 percent solids solution of polyelectrolyte containing 52 mole percent unsaponified ethyl acrylate was prepared by treating 100 g of the latex of Step 1 (diluted with 40 g $H_2O$) with 14.3 g of 50% NaOH (diluted with 29.5 g $H_2O$). The mixture was held at 55°C. for 18 hours to produce a viscous lightly colored solution. Acetic acid (10 percent by weight dissolved polymer) was added for the final pH near 5.

Step 3 — Film Forming

The acidified solution of Step 2 was cast on a chrome plate, dried under heat lamps, and cured in a 150°C. oven for 60 minutes. The polymer absorbency (gel capacity) in 0.27 N NaCl solution was 16 (expressed as grams fluid imbibed per gram dry polymer).

As a control, Example 1 was repeated using only 0.25 weight percent N-isobutoxymethacrylamide in the monomer feed. This level of built-in curing agent is too low as a soluble polymer rather than a swellable polymer resulted after following the procedure of Example 1.

EXAMPLE 2

Example 1 was repeated using 1.0 g N-isobutoxymethacrylamide, (0.5 percent by weight of monomer feed) 169 g ethyl acrylate, and 30 g methacrylic acid as Part B of the polymerization recipe. The resulting latex was digested at 40°C. for 1 hour, had practically no coagulum and was 39 percent solids. Following the procedure of Example 1, an absorbent polymer with a 29.4 gel capacity was produced.

EXAMPLE 3

Example 2 was repeated using 2.0 g. N-isobutoxymethacrylamide (1.0 percent by weight of monomer feed), 168 g ethyl acrylate, and 30 g methacrylic acid as Part B of the polymerization recipe. The resulting latex had little coagulum (1.7 percent of monomer feed) and was 39.26 percent solids. Following the procedure of Example 1, an absorbent polymer with a 25.6 gel capacity was produced.

I claim:

1. A solution useful to form water swellable articles of a carboxylic synthetic polyelectrolyte upon curing which comprises
   1. a solvent selected from the group consisting of water, lower alcohols and mixtures thereof,
   2. about 5 to about 60% by weight based on (1) of a crosslinkable carboxylic copolymer which contains in the copolymer
      A. about 25 to about 98% by weight based on the total weight of the copolymer of an alkali metal salt of an olefinically unsaturated monocarboxylic acid;
      B. about 2 to about 50% by weight of an olefinically unsaturated monocarboxylic acid;
      C. about 25 to about 60% by weight of an alkyl ester of an olefinically unsaturated monocarboxylic acid and
      D. about 0.3 to about 5.0% by weight of crosslinking units of an N-substituted acrylamide or methacrylamide having the formaula $H_2C=CR—C(O)—NHCH_2—O—R'$ wherein R is selected from hydrogen or methyl and R' is hydrogen or an alkyl group of 1–8 carbons.

2. The solution as set forth in claim 1 wherein the crosslinking agent is N-isobutoxymethyl acrylamide.

3. A method of preparing a water swellable polyelectrolyte which comprises the steps of
   1. preparing a composition as set forth in claim 1,
   2. evaporating about 75 percent of the solvent therefrom to obtain a substantially dry crosslinked water-swellable polyelectrolyte.

4. A method of preparing a swellable polyelectrolyte which comprises the steps of
   1. preparing a composition as set forth in claim 2,
   2. evaporating about 75 percent of the solvent therefrom to obtain a substantially dry crosslinked water-swellable polyelectrolyte.

* * * * *